United States Patent
Kimura et al.

(10) Patent No.: US 8,373,006 B2
(45) Date of Patent: Feb. 12, 2013

(54) ANTI-LEISHMANIAL COMPOUND AND ANTI-LEISHMANIAL DRUG

(75) Inventors: Junji Kimura, Sagamihara (JP); Shohei Horie, Ibaraki (JP); Harumi Marushima, Yokosuka (JP); Yoshitsugu Matsumoto, Taito-Ku (JP); Chizu Sanjoba, Kawaguchi (JP); Yasutaka Osada, Bunkyo-bu (JP)

(73) Assignee: Aoyama Gakuin Educational Foundation, Tokyo (JP)

( * ) Notice: Subject to any disclaimer, the term of this patent is extended or adjusted under 35 U.S.C. 154(b) by 0 days.

(21) Appl. No.: 13/146,366

(22) PCT Filed: Mar. 8, 2011

(86) PCT No.: PCT/JP2011/055292
§ 371 (c)(1),
(2), (4) Date: Nov. 1, 2011

(87) PCT Pub. No.: WO2012/053232
PCT Pub. Date: Apr. 26, 2012

(65) Prior Publication Data
US 2012/0095257 A1    Apr. 19, 2012

(30) Foreign Application Priority Data
Oct. 19, 2010   (JP) .................. 2010-234923

(51) Int. Cl.
C07C 403/02   (2006.01)
C07C 59/82    (2006.01)
A61K 31/202   (2006.01)
A61P 33/02    (2006.01)

(52) U.S. Cl. ..................................... 562/508
(58) Field of Classification Search .......... None
See application file for complete search history.

(56) References Cited

U.S. PATENT DOCUMENTS
2012/0095257 A1   4/2012   Kimura et al.

FOREIGN PATENT DOCUMENTS
| JP | A-2004-331545 | 11/2004 |
| JP | A-2006-321728 | 11/2006 |
| JP | B1-4762381    | 8/2011  |
| WO | WO 2006/011394 A1 | 2/2006 |

OTHER PUBLICATIONS

Sato J. Toxicol.—Toxin Reviews, 1996, 15(2), 171-198.*

Freile-Pelegrin et al., "Antileishmanial properties of tropical marine algae extracts," *Fitoterapia*, 2008, vol. 79, pp. 374-377.
Jung et al., "Meroditerpenoids from the Brown Alga *Sargassum siliquastrum*," *J. Nat. Prod.*, 2008, vol. 71, pp. 1714-1719.
International Search Report in International Application No. PCT/JP2011/055292; dated Apr. 5, 2011 (with English-language translation).
Horie et al; "Antibacterial Quinone Metabolites from the Brown Alga, *Sargassum sagamianum*;" Bulletin of the Chemical Society of Japan; Mar. 2008; vol. 81, No. 9.; pp. 1125-1130.
The 88th Annual Meeting of the Chemical Society of Japan in Spring Koen Yokoshu II; 2008; Lecture No. 2 PC-019; pp. 1488.
Kusumi et al.; "Structures of New Plastoquinones from the Brown Alga *Sargassum serratifolium*;" Chemistry Letters; Jan. 1979; pp. 277-278.
Segawa et al.; "New Plastoquinones from the Brown Alga *Sargassum sagamianum* var. *yezoense*;" Chemistry Letters; Apr. 1987; pp. 1365-1366.
Tziveleka et al.; "Marine Polyprenylated Hydroquinones, Quinones, and Chromenols with Inhibitory Effects on Leukotriene Formation;" Chemistry & Biodiversity; 2005; vol. 2, No. 7; pp. 901-909.
Ishitsuka et al.; "New Geranylgeranylbenzoquinone Derivatives from *Sargassum tortile*;" Chemistry Letters; Aug. 1979; pp. 1269-1272.
Fukui et al.; "Total Synthesis of Antibacterial Quinone Isolated from *Sargassum sargamianum*;" The 54th Symposium on the Chemistry of Terpenes, Essential Oils, and Aromatics; Oct. 2010; Lecture No. 1P II-7; pp. 102-104.
Dec. 13, 2011 International Search Report issued in International Patent Application No. PCT/JP2011/073482.
Kimura et al; U.S. Appl. No. 13/583,345, filed Oct. 4, 2012.
Oct. 8, 2012 Office Action issued in Korean Patent Application No. KR2012-7020093 (with translation).
Nahas et al; "Radical-Scavenging Activity of Aegean Sea Marine Algae;" Food Chemistry; 2007; vol. 102; pp. 577-581.

* cited by examiner

*Primary Examiner* — Yevegeny Valenrod
(74) *Attorney, Agent, or Firm* — Oliff & Berridge, PLC

(57) ABSTRACT

Provided is an anti-leishmanial compound represented by formula (3):

{Chem. 4}

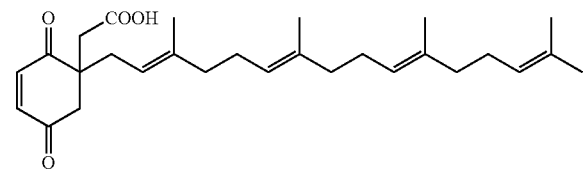

(3)

2 Claims, 10 Drawing Sheets

ANTI-LEISHMANIAL COMPOUND AND ANTI-LEISHMANIAL DRUG

TECHNICAL FIELD

The present invention relates to an anti-leishmanial compound having a high anti-leishmanial activity, and an anti-leishmanial drug.

BACKGROUND ART

Leishmaniasis is an infectious disease caused by becoming infected with the genus *Leishmania*. Leishmaniasis has been designated as one of six major tropical diseases by the World Health Organization (WHO). Leishmaniasis is vector-borne disease by the bite of blood-sucking sandfly vectors, resulting in the parasite inoculation to mammalian hosts. The symptoms of Leishmaniasis is fatal in severe ranging from mild to heal, but pentavalent antimony formulations have been used primarily as a treatment known to cause severe adverse side effects. Therefore, there is a demand for a new drug having a low risk of adverse side effects. Furthermore, AmBisome has been developed as a drug suppressing the adverse side effects, but this drug has a problem that the drug is expensive.

On the other hand, it has been reported that marine algae-derived metabolites exhibit an anti-leishmanial activity (see, for example, Non-Patent Document 1). However, this document does not specify which compound derived from marine algae would have an anti-leishmanial activity.

CITATION LIST

{Non Patent Literature}
{NPL 1} Y. Freile-Pelegrin, D. Robledo, M. J. Chan-Bacab, B. O. Orrtega-Morales, "Antileishmanial properties of tropical marine algae extract," Fitoterapia (Holland), Elsevier, 2008, 79, p. 374 to 377

SUMMARY OF INVENTION

Technical Problem

The inventors of the present invention conducted a thorough investigation, and as a result, they paid attention to Sargassum yamadae, a brown alga in the Family Sargassaceae of the Order Fucales, and attempted fractionation of an extract of the alga. Accordingly, the inventors found that the extract has a high anti-leishmanial activity, and thus completed the present invention.

Solution to Problem

That is, the anti-leishmanial compound according to the present invention is represented by formula (3):

{Chem. 1}

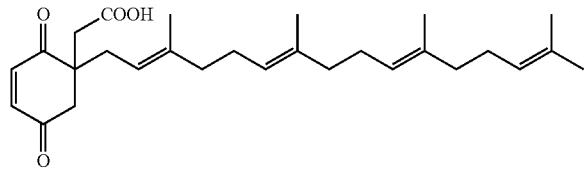

(3)

Furthermore, the anti-leishmanial drug according to the present invention is characterized by containing the compound represented by the formula (3) and a pharmacologically acceptable salt thereof as active ingredients.

ADVANTAGEOUS EFFECT OF INVENTION

According to the present invention, an anti-leishmanial compound having a high anti-leishmanial activity and an anti-leishmanial drug can be provided.

DESCRIPTION OF EMBODIMENTS

Figure 1:
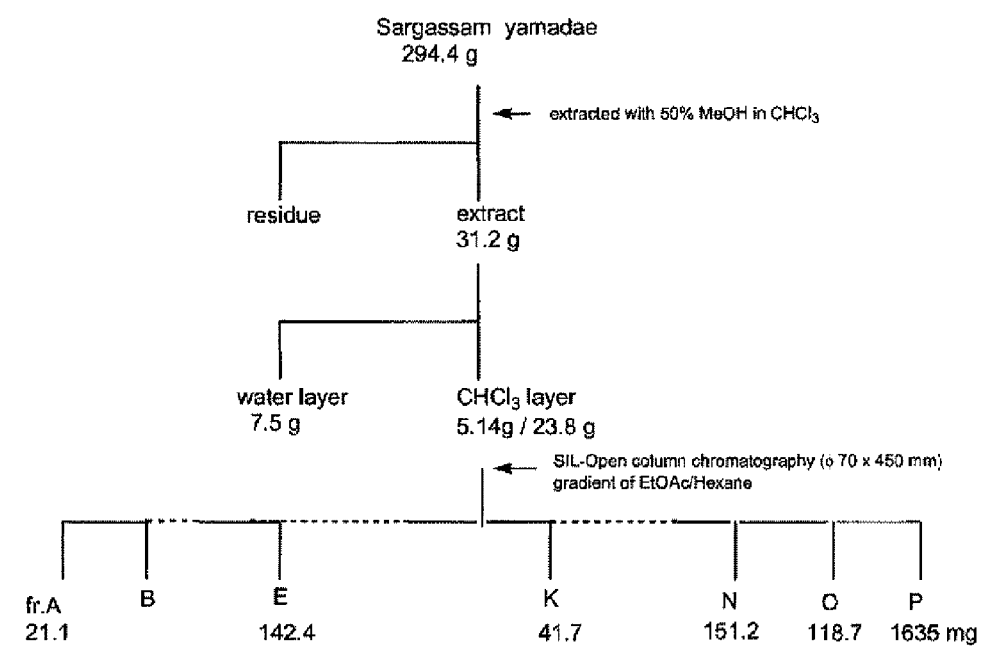
FIG. 1 is a diagram showing the procedure of an operation for separation of compounds (first operation) according to the Example of the present invention.

Hereinafter, the anti-leishmanial compound and the anti-leishmanial drug according to embodiments of the present invention will be described with reference to the attached drawings. The anti-leishmanial compound according to the present invention is at least one of the compounds represented by formulas (1) to (6), and the anti-leishmanial drug according to the present invention contains at least one of the compounds represented by the formulas (1) to (6) as an active ingredient.

{Chem. 2}

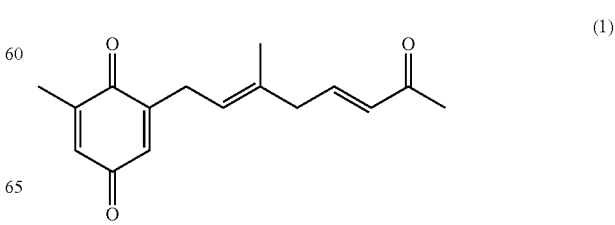

(1)

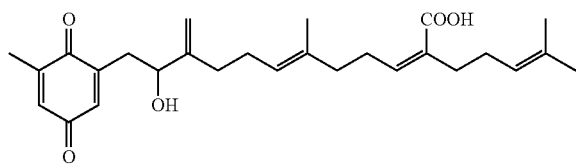

(2)

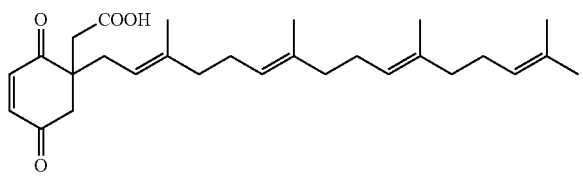

(3)

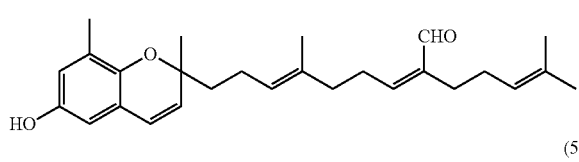

(4)

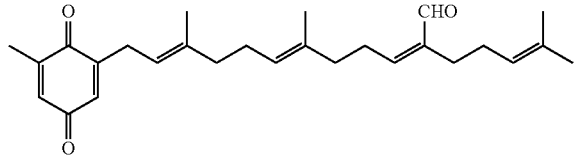

(5)

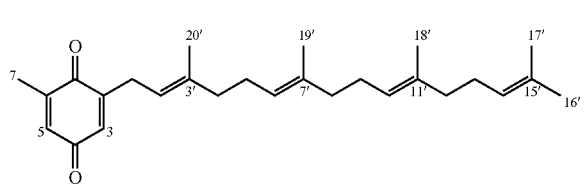

(6)

In order to recover anyone of the compounds represented by the formulas (1) to (6), those means for separation and purification that are typically used to collect metabolites may be appropriately utilized on the algae such as brown algae, while taking into consideration of the physicochemical properties of the relevant compound. For example, an extraction operation is carried out on the algae, using an organic solvent, preferably an equivolume solvent mixture of chloroform-methanol. Subsequently, the compound may be further extracted from the extract thus obtained, using an organic solvent such as dichloromethane, or the compound may be adsorbed and eluted using various chromatographic techniques. Furthermore, if necessary, further purification operations may be carried out to recover the compound with a desired purity. In regard to the chromatographic techniques, conventionally used inorganic and organic carriers, for example, silica gel and a polystyrene resin, can be used as the carrier.

The compounds represented by the formulas (1) to (6) are useful as, for example, antiprotozoal drugs, particularly as anti-leishmanial drugs, in the field of pharmaceuticals. A compound represented by any one of the formulas (1) to (6) may be used singly, or may be mixed with additives that are generally acceptable in formulations and formulated into preparations. Examples of dosage forms include dosage forms using peroral preparations such as tablets, granules, capsules, pills, powders, liquids, suspensions, emulsions, syrups, elixirs, and extracts; and dosage forms using parenteral preparations such as injectable preparations, liquids, suppositories, ointments, patches, poultices, and lotions. However, there are no particular limitations on the dosage form, and the dosage form can be appropriately selected in accordance with the purpose of therapy, or the like.

In the case of tablets, granules, pills, capsules and powders, additives such as an excipient, a binder, a disintegrant, a lubricating agent can be incorporated therein. Examples of the excipient include starch, carboxymethyl cellulose, sucrose, dextrin, and corn starch.

Examples of the binder include crystalline cellulose, crystalline cellulose carmellose sodium, methylcellulose, hydroxypropyl cellulose, low-substituted hydroxypropyl cellulose, hydroxypropylmethyl cellulose, hydroxypropylmethyl cellulose phthalate, hydroxypropylmethyl cellulose acetate succinate, carmellose sodium, ethyl cellulose, carboxymethylethyl cellulose, hydroxyethyl cellulose, wheat starch, rice starch, corn starch, potato starch, dextrin, pregelatinized starch, partially pregelatinized starch, hydroxypropyl starch, pullulan, polyvinylpyrrolidone, aminoalkyl methacrylate copolymer E, aminoalkyl methacrylate copolymer RS, methacrylic acid copolymer L, methacrylic acid copolymer, polyvinylacetal diethylaminoacetate, polyvinyl alcohol, gum arabic, powdered gum arabic, agar, gelatin, white shellac, tragacanth, purified sucrose, and macrogol.

Examples of the disintegrant include crystalline cellulose, methyl cellulose, low-substituted hydroxypropyl cellulose, carmellose, carmellose calcium, carmellose sodium, croscarmellose sodium, wheat starch, rice starch, corn starch, potato starch, partially pregelatinized starch, hydroxypropyl starch, carboxymethyl starch sodium, and tragacanth.

Examples of the lubricating agent include wheat starch, rice starch, corn starch, stearic acid, calcium stearate, magnesium stearate, hydrated silicon dioxide, light silicic anhydride, synthetic aluminum silicate, dry aluminum hydroxide gel, talc, magnesium metasilicate aluminate, calcium hydrogen phosphate, anhydrous calcium hydrogen phosphate, sucrose fatty acid esters, waxes, hydrogenated vegetable oils, and polyethylene glycol.

Furthermore, in the case of liquids, syrups, suspensions, emulsions, and elixirs, a colorant, a taste-masking agent, a flavoring agent and the like may be incorporated as additives, in addition to inert diluents that are generally used, such as water and vegetable oils.

In the case of injectable preparations, additives such as a suspension liquid, an emulsion liquid, and a ready-to-use solubilizing agent can be incorporated. Furthermore, in the case of ointments and suppositories, fats, fatty oil, lanolin, petrolatum, paraffin, waxes, resins, plastics, a base, a glycol, a higher alcohol, water, an emulsifier, a suspending agent, and the like can be incorporated as additives. In the case of poultices, glycerin, water, a water-soluble polymer, a water-absorptive polymer, and the like can be incorporated as additives. In the case of lotions, a solvent, an emulsifier, a suspending agent, and the like can be incorporated as additives.

The anti-leishmanial compound of the present invention can be added to a food product, a chewing gum, a beverage or the like, and then be incorporated into so-called foods for specified health uses (for example, anti-leishmanial foods), dietary supplements, and the like.

As well, the compounds represented by the formulas (1) to (6) as described above are conceptually considered to include pharmacologically acceptable salts of these compounds. That is, the present invention includes biochemical precursors that are converted to the compounds and amides by metabolism in the body of a human being or an animal, and exhibit a pharmacological activity. According to the present invention, the term pharmacologically acceptable salt is a salt that is obtained by treating one of the compounds described above with an acid or a base, and means a salt which does not have significant toxicity and can be used as a medicine. Examples of such an acid addition salt include addition salts based on inorganic acids such as hydrochloric acid, hydrobromic acid, sulfuric acid, and phosphoric acid; and organic acids such as maleic acid, fumaric acid, tartaric acid, and citric acid. Examples of a salt based on a base include salts based on alkali metal hydroxides such as sodium hydroxide and potassium hydroxide; alkaline earth metal hydroxides such as calcium hydroxide and magnesium hydroxide; and organic bases such as guanidine, triethylamine, and dicyclohexylamine.

EXAMPLES

Hereinafter, the present invention will be more specifically described by way of Examples.
1. Operation for Separation of Compounds Represented By Formulas (1) to (6)
(1) Extraction of Lipid Components
Sargassum yamadae (294.4 g), a brown alga in the Family Sargassaceae of the Order Fucales, was immersed for one day in an equivolume solvent mixture (1.4 L) of methanol and chloroform. The residue was removed by suction filtering, and lipid components were extracted. This residue was further immersed for one day in an equivolume solvent mixture (1.4 L) of methanol and chloroform, and lipid components were extracted by performing suction filtration. The solvent was removed under reduced pressure, and the extract (31.2 g) thus obtained was partitioned into two layers using water and chloroform. Thus, lipid components (23.8 g) were obtained. In addition, Sargassum was washed with artificial seawater after collection, dried in a constant temperature dehumidification chamber, pulverized, and then stored at −20° C. until used in experiments.
(2) First Operation of Separation
Among the lipid components obtained by the operation described in section (1), 5.14 g was fractionated into sixteen fractions, such as fraction A to fraction P, by open column chromatography (Φ7×45 cm) while the proportion of the solvent of an ethyl acetate-hexane system was varied, as shown in FIG. 1.

Among these, as shown in FIG. 2 to FIG. 5, Fractions E, K, N and O were further subjected to open column chromatography, thin layer chromatography, and HPLC using an ethyl acetate-hexane mixed eluate, and thus various kinds of compounds were separated.

Figure 2:
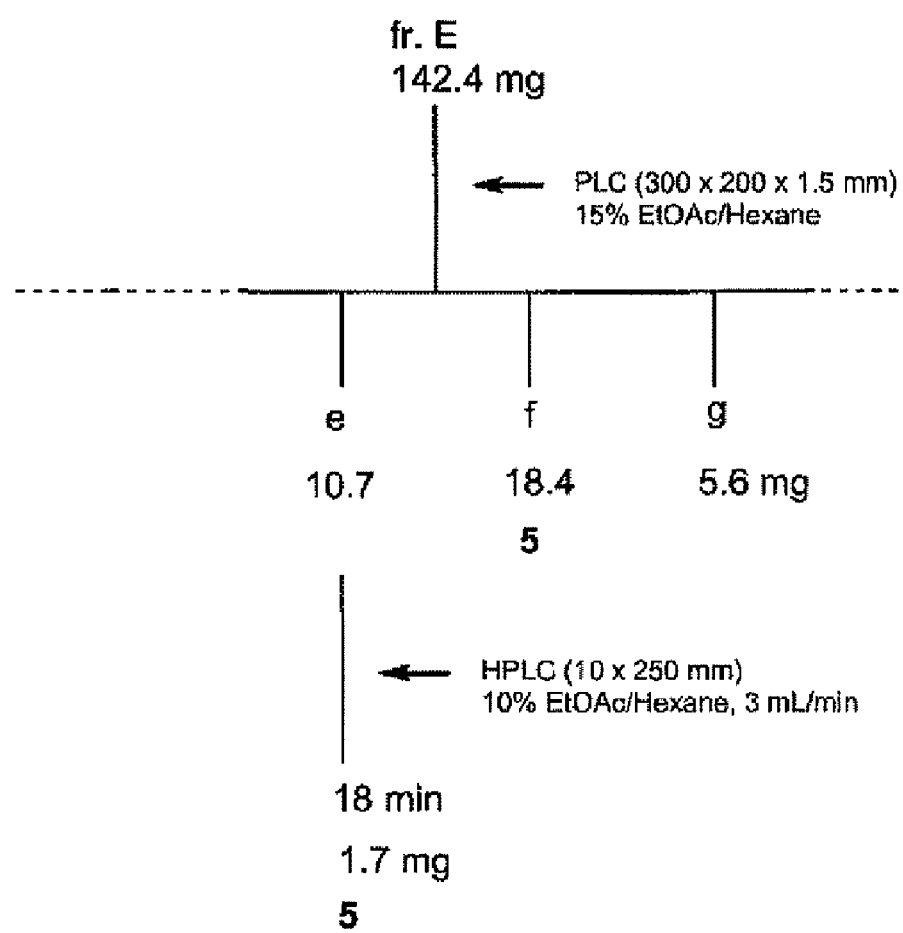
FIG. 2 is a diagram showing the procedure of an operation for separation of compounds (first operation) according to the Example of the present invention.

As shown in FIG. 2, the fraction E was subjected to thin layer chromatography, and various kinds of fractions were obtained.

Among these, a compound represented by formula (5) was obtained from fraction f. Further, fraction e was subjected to HPLC, and the compound represented by the formula (5) was obtained at a retention time of 18 minutes. As well, in FIGS. 2 to 8, the masses (mg) of the fractions thus obtained are indicated below the fraction names. Furthermore, in the case of any of the compounds represented by the formulas (1) to (6), the numeral of the formula of the relevant compound is indicated in a bold letter. For the fractions obtained by performing HPLC, the retention time and the mass (mg) of the compound thus obtained are indicated in order from the top, and in the case of any of the compounds represented by the formulas (1) to (6), the numeral of the formula of the relevant compound is indicated in a bold letter.

Figure 3:
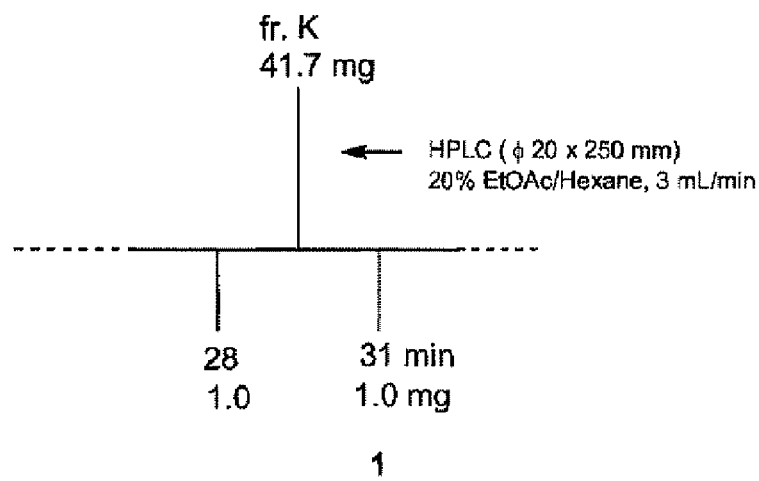
FIG. 3 is a diagram showing the procedure of an operation for separation of compounds (first operation) according to the Example of the present invention.
Figure 4:
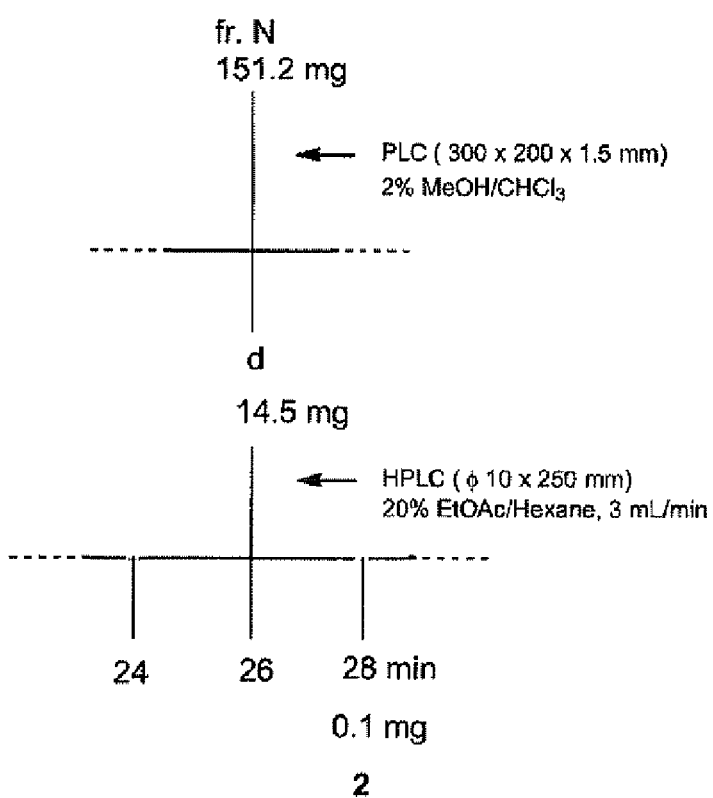
FIG. 4 is a diagram showing the procedure of an operation for separation of compounds (first operation) according to the Example of the present invention.
Figure 5:
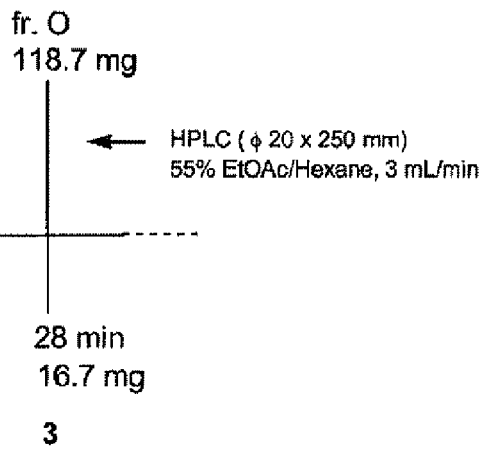
FIG. 5 is a diagram showing the procedure of an operation for separation of compounds (first operation) according to the Example of the present invention.
Figure 6:
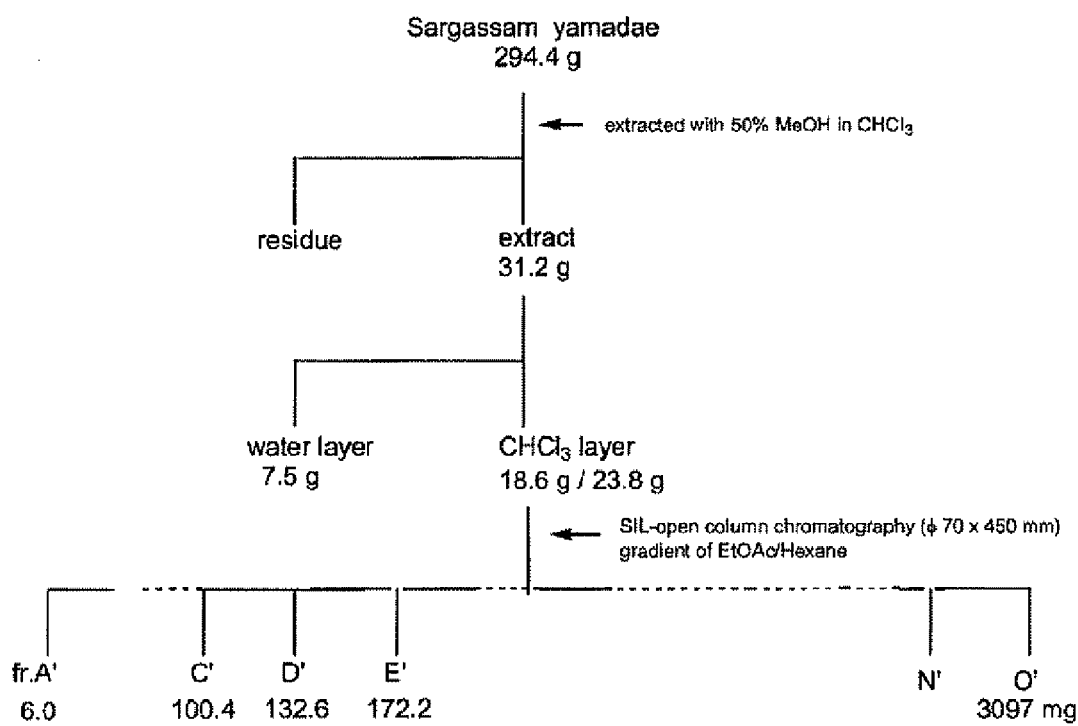
FIG. 6 is a diagram showing the procedure of an operation for separation of compounds (second operation) according to the Example of the present invention.

Furthermore, as shown in FIG. 3, the fraction K was subjected to HPLC using a 20% ethyl acetate-hexane eluate, and sargaquinoic acid was obtained at a retention time of 28 minutes, while the compound represented by the formula (1) was obtained at a retention time of 31 minutes. As shown in FIG. 4, the fraction N was subjected to thin layer chromatography and HPLC using a 20% ethyl acetate-hexane eluate, and the compound represented by the formula (2) (HREIMS m/z 440.2560 {M+}, $C_{27}H_{36}O_5$ (Δ−0.3 mmu)) was obtained during HPLC at a retention time of 28 minutes. Furthermore, as shown in FIG. 5, the fraction O was subjected to HPLC using a 55% ethyl acetate-hexane eluate, and the compound represented by the formula (3) (HREIMS m/z 440.2934 {M+}, $C_{28}H_{40}O_4$ (Δ+0.8 mmu) was obtained at a retention time of 28 minutes.
(3) Second Operation of Separation
Among the lipid components obtained by the extraction operation of lipid components as described above, the remaining 18.6 g, which was not used in the first operation of separation, was fractionated into fifteen fractions, such as fraction A' to fraction O', by open column chromatography (Φ7×45 cm) as shown in FIG. 6, while the proportion of the solvent of an ethyl acetate-hexane system was varied.

Figure 7:
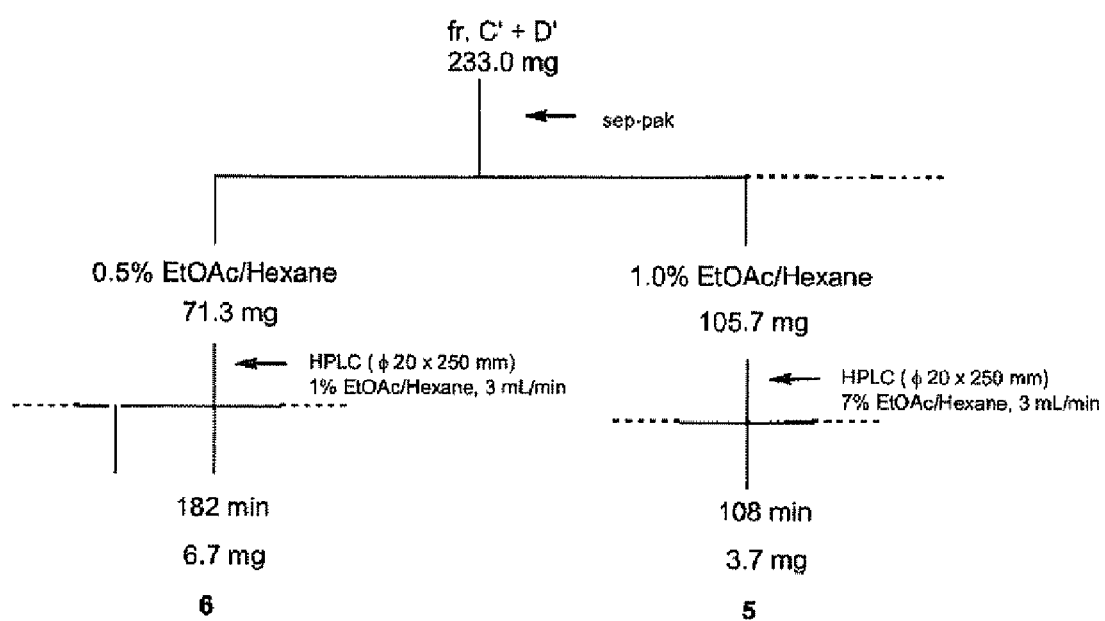
FIG. 7 is a diagram showing the procedure of an operation for separation of compounds (second operation) according to the Example of the present invention.

As shown in FIG. 7, among the fractions thus obtained, fraction C' and fraction D' were combined, and the mixture was subjected to extraction by means of Sep-Pak. A fraction which had been extracted using a 0.5% ethyl acetate-hexane mixed eluate, was subjected to HPLC using a 1% ethyl acetate-hexane eluate, and the compound represented by the formula (6) was obtained at a retention time of 182 minutes. Furthermore, a fraction which had been extracted using a 1% ethyl acetate-hexane mixed eluate, was subjected to HPLC using a 7% ethyl acetate-hexane eluate, and the compound represented by the formula (5) was obtained at a retention time of 108 minutes.

Figure 8:
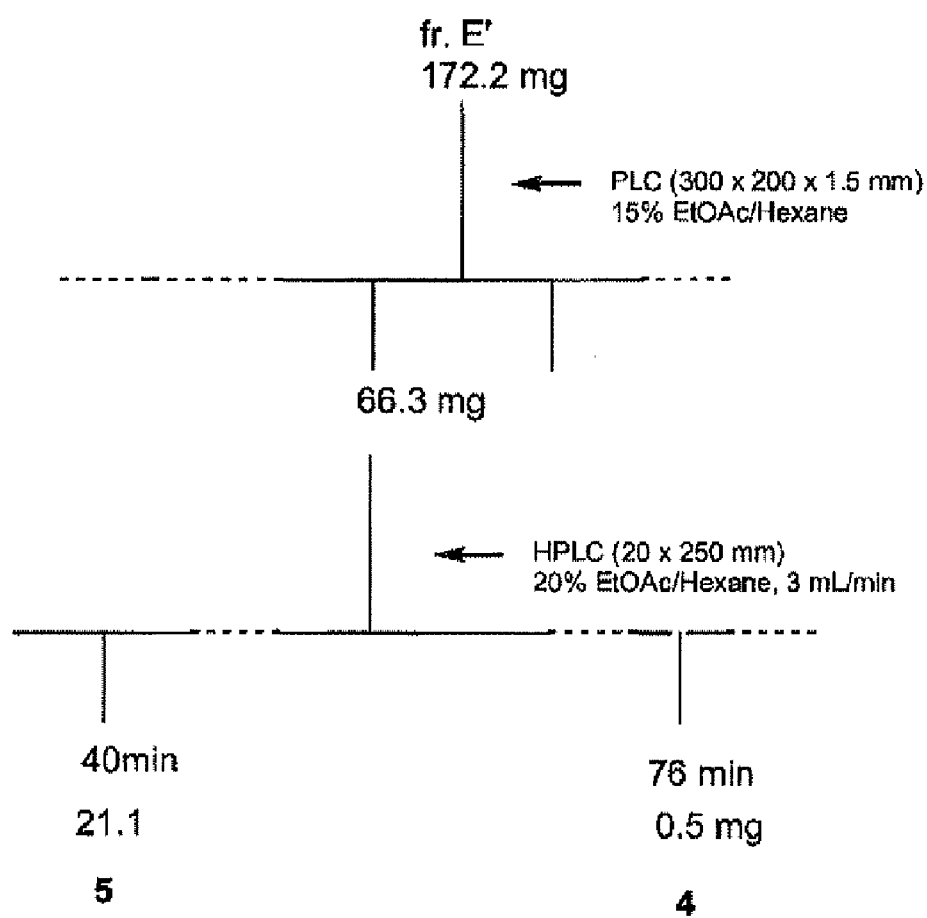
FIG. 8 is a diagram showing the procedure of an operation for separation of compounds (second operation) according to the Example of the present invention.

As shown in FIG. 8, the fraction E' was subjected to thin layer chromatography, and was further subjected to HPLC using a 20% ethyl acetate-hexane mixed eluate. The compound represented by the formula (5) was obtained at a retention time of 40 minutes, and the compound represented by the formula (4) (EIMS m/z 408 $C_{27}H_{36}O_3$ {M+}, m/z 175 {M−$C_{15}H_{25}O$}) at retention time of 76 minutes.

The compounds thus obtained were subjected to an analysis of the molecular structures by $^1$H-NMR, $^{13}$C-NMR and the like. The NMR spectral data are presented in the Tables below. As well, the NMR data of the compound represented by the formula (1) are presented together with the NMR data published in Bull. Chem. Soc. Jpn., 2008, 81(9), 1125 to 1130, and the NMR data of the compound represented by the formula (4) are presented together with the NMR data of sargachromenol, which has a similar structure. The NMR data of the compounds represented by the formulas (5) and (6) are presented together with the NMR data of sargaquinoic acid.

TABLE 1

NMR data of compound represented by formula (1)

| | (1) | | | literature | |
|---|---|---|---|---|---|
| # | $δ_H$ | J (Hz) | $δ_C$ | $δ_H$ | J (Hz) |
| 1 | | | 187.8 | | |
| 2 | | | 147.8 | | |
| 3 | 6.47 d | 1.8 | 132.5 | 6.47 m | |

TABLE 1-continued

NMR data of compound represented by formula (1)

| | (1) | | | literature | |
|---|---|---|---|---|---|
| # | $\delta_H$ | J (Hz) | $\delta_C$ | $\delta_H$ | J (Hz) |
| 4 | | | 187.8 | | |
| 5 | 6.56 m | | 133.2 | 6.57 dq | 1.8, 1.4 |
| 6 | | | 146.0 | | |
| 7 | 2.07 d | 1.4 | 16.0 | 2.07 d | 1.4 |
| 1' | 3.17 d | 7.3 | 27.8 | 3.16 br. d | 7.3 |
| 2' | 5.24 br. d | 7.3 | 121.2 | 5.24 tq | 7.3, 1.4 |
| 3' | | | 136.2 | | |
| 4' | 2.94 d | 7.3 | 42.4 | 2.94 br. d | 6.9 |
| 5' | 6.75 td | 6.9, 16.0 | 145.0 | 6.75 td | 6.9, 16.0 |
| 6' | 6.09 br. d | 16.0 | 132.5 | 6.09 dt | 16.0, 1.4 |
| 7' | | | 198.3 | | |
| 8' | 2.27 | | 27.1 | 2.26 s | |
| 9' | 1.67 br. s | | 16.4 | 1.67 br. s | |

* not determined

TABLE 2

NMR data of compound represented by formula (2)

| # | $\delta_C$ | $\delta_H$ | | J(Hz) | HMBC(C) |
|---|---|---|---|---|---|
| 1 | 187.7 | | | | |
| 2 | 145.8 | | | | |
| 3 | 134.6 | 6.64 | br.d | 2.7 | |
| 4 | 188.4 | | | | |
| 5 | 133.3 | 6.57 | m | | |
| 6 | 145.9 | | | | |
| 7 | 16.1 | 2.05 | d | 1.4 | 1, 5, 6 |
| 1' | 36.0 | 2.78 | dd | 14.2, 3.7 | 2, 3, 2' |
| | | 2.54 | dd | 14.2, 7.1 | |
| 2' | 73.3 | 4.26 | dd | 8.7, 3.7 | 2' |
| 3' | 150.8 | | | | |
| 4' | 26.4 | 2.18 | overlapped | | 5' |
| 5' | 31.7 | 2.20 | overlapped | | 4', 20' |
| 6' | 124.3 | 5.15 | dq | 6.4, 0.9 | |
| 7' | 135.0 | | | | |
| 8' | 39.0 | 2.08 | overlapped | | 6' |
| 9' | 28.3 | 2.58 | q | 7.3 | 10', 11' |
| 10' | 144.0 | 5.95 | t | 7.3 | 8', 12' |
| 11' | 130.5 | | | | |
| 12' | 34.6 | 2.27 | t | 7.8 | 13', 14' |
| 13' | 27.9 | 2.14 | overlapped | | |
| 14' | 123.4 | 5.10 | overlapped | | |
| 15' | 132.3 | | | | |
| 16' | 25.6 | 1.68 | s | | 17' |
| 17' | 17.7 | 1.58 | s | | 16' |
| 18' | 166.0 | | | | |
| 19' | 16.1 | 1.62 | s | | 6', 7', 8' |
| 20' | 110.2 | 5.08 | s | | 4' |
| | | 4.90 | s | | |

TABLE 3

NMR data of compound represented by formula (3)

| | (3) | | | | |
|---|---|---|---|---|---|
| # | $\delta_C$ | $\delta_H$ | | J(Hz) | HMBC(C) |
| 1 | 200.7 | | | | |
| 2 | 50.2 | | | | |
| 3 | 46.5 | 2.72 | d | 16.5 | 1, 2, 4, 5 |
| | | 3.28 | d | 16.5 | 1, 2, 4, 5 |
| 4 | 197.4 | | | | |
| 5 | 140.8 | 6.69 | d | 10.5 | 4, 6 |
| 6 | 139.9 | 6.72 | d | 10.5 | 1, 2, 5 |
| 1' | 38.2 | 2.21 | dd | 7.8, 13.7 | 1, 2, 2', 3' |
| | | 2.31 | dd | 8.2, 13.7 | 1, 2, 2', 3' |
| 2' | 116.7 | 4.95 | dd | 7.8, 8.2 | 4', 20' |

TABLE 3-continued

NMR data of compound represented by formula (3)

| | (3) | | | |
|---|---|---|---|---|
| # | $\delta_C$ | $\delta_H$ | J(Hz) | HMBC(C) |
| 3' | 141.6 | | | |
| 4' | 39.7 | 1.97 m | | 2', 3', 5', 6' |
| 5 | 26.7 | 2.04 m | | 3', 4', 6', 7' |
| 6' | 124.6 | 5.06 t | 6.9 | 4' |
| 7' | 135.5 | | | |
| 8' | 39.6 | 1.98 m | | 6', 7', 9', 19' |
| 9' | 26.6 | 2.05 m | | 8', 10', 11' |
| 10' | 124.1 | 5.10 t | 6.9 | 8', 18' |
| 11' | 135.0 | | | |
| 12' | 39.9 | 1.95 m | | 10', 11', 13', 18' |
| 13' | 26.3 | 2.05 m | | 11', 12', 14', 15' |
| 14' | 124.4 | 5.10 t | 6.9 | 12', 16', 17' |
| 15' | 131.3 | | | |
| 16' | 25.7 | 1.68 s | | 14', 15', 17' |
| 17' | 17.6 | 1.60 s | | 14', 15', 16' |
| 18' | 16.0 | 1.58 s | | 10' |
| 19' | 16.0 | 1.58 s | | 7' |
| 20' | 16.4 | 1.53 s | | 3' |
| 21' | 39.7 | 2.33 d | 17.9 | 1, 2, 22' |
| | | 3.09 d | 17.9 | |
| 22' | 176.0 | | | |

TABLE 4

NMR data of compound represented by formula (4)

| | (4) | | | | sarga-chromenol | |
|---|---|---|---|---|---|---|
| # | $\delta_C$ | $\delta_H$ | J (Hz) | HMBC (C) | $\delta_c$ | $\delta_H$ |
| 2 | 77.7 | | | | 77.6 | |
| 3 | 130.6 | 5.57 d | 9.6 | 2, 4a | 130.4 | 5.57 |
| 4 | 122.9 | 6.26 d | 9.6 | 2, 4a, 5, 8a | 122.9 | 6.24 |
| 4a | 121.3 | | | | 121.2 | |
| 5 | 110.3 | 6.33 d | 2.7 | 4, 7, 8a | 110.3 | 6.32 |
| 6 | 148.5 | | | | 148.9 | |
| 7 | 117.1 | 6.47 d | 2.7 | 5, 8a, 9 | 117.1 | 6.48 |
| 8 | 126.3 | | | | 126.1 | |
| 8a | 144.9 | | | | 144.5 | |
| 9 | 15.5 | 2.14 s | | 7, 8, 8a | 15.4 | 2.13 |
| 10 | 25.9 | 1.37 s | | 2, 3, 1' | 25.8 | 1.36 |
| 1' | 40.7 | 1.68 overlapped | | 2, 10, 2' | 40.7 | 1.68 |
| 2' | 22.6 | 2.15 overlapped | | 1', 3' | 22.5 | 2.1 * |
| 3' | 125.5 | 5.16 br. t | 7.3 | 2', 5', 16' | 124.9 | 5.15 |
| 4' | 133.6 | | | | 134.2 | |
| 5' | 38.3 | 2.12 t | 7.3 | 4', 6', 7', 16' | 39.0 | 2.07 |
| 6' | 27.0 | 2.43 br. q | 7.3 | 4', 5', 7', 8' | 28.0 | 2.60 |
| 7' | 155.5 | 6.41 t | 7.3 | 5', 6', 9', 15' | 145.3 | 6.00 |
| 8' | 143.2 | | | | 130.6 | |
| 9' | 24.2 | 2.25 br. t | 7.8 | 7', 8', 10', 15' | 34.4 | 2.27 |
| 10' | 27.4 | 2.03 br. q | 7.3 | 8', 9', 12' | 27.8 | 2.13 |
| 11' | 123.6 | 5.09 tt | 7.3, 1.4 | 13', 14' | 123.4 | 5.09 |
| 12' | 133.6 | | | | 132.1 | |
| 13' | 25.7 | 1.67 s | | 11', 12', 14' | 25.5 | 1.68 |
| 14' | 17.6 | 1.56 s | | 11', 12', 13' | 17.6 | 1.59 |
| 15' | 195.2 | 9.34 s | | 8' | 173.0 | |
| 16' | 15.8 | 1.60 s | | 3', 4', 5' | 15.6 | 1.58 |

* not determined

TABLE 5

NMR data of compound represented by formula (5)

| | (5) | | | | sargaquinoic acid | |
|---|---|---|---|---|---|---|
| # | $\delta_C$ | $\delta_H$ | J (Hz) | HMBC (C) | $\delta_C$ | $\delta_H$ |
| 1 | 187.9 | | | | 187.9 | |
| 2 | 154.9 | | | | 148.4 | |
| 3 | 133.1 | 6.45 dt | 2.3, 1.8 | 1 or 4 | 132.2 | 6.46 |
| 4 | 188.0 | | | | 188.0 | |
| 5 | 133.9 | 6.54 br. q | 1.4 | | 133.1 | 6.54 |
| 6 | 148.4 | | | | 145.9 | |
| 7 | 16.0 | 2.06 d | 1.4 | 1, 5, 6 | 15.9 | 2.05 |
| 1' | — | 3.13 d | 7.3 | 1, 2, 3, 2', 3' | — | 3.13 |
| 2' | 118.2 | 5.15 br. t | 7.3 | | 118.0 | 5.15 |
| 3' | 143.2 | | | | 139.7 | |
| 4' | 39.5 | 2.1 * overlapped | | | 39.5 | 2.1 |
| 5' | 25.7 | 2.1 * overlapped | | | 26.3 | 2.1 |
| 6' | 125.1 | 5.09 br. t | 7.3 | | 124.4 | 5.12 |
| 7' | 139.7 | | | | 134.5 | |
| 8' | 38.3 | 2.1 * overlapped | | | 39.0 | 2.1 |
| 9' | 27.4 | 2.45 q | 7.3 | 8', 10', 15' | 28.1 | 2.60 |
| 10' | 145.9 | 6.41 t | 7.3 | 4', 8' | 145.1 | 6.01 |
| 11' | 132.3 | | | | 130.7 | |
| 12' | 27.5 | 2.26 t | 7.3 | 10', 15' | 34.5 | 2.26 |
| 13' | 27.0 | 2.1 * overlapped | | | 27.8 | 2.1 |
| 14' | 123.6 | 5.15 br. t | 7.3 | | 123.4 | 5.09 |
| 15' | 132.3 | | | | 132.1 | |
| 16' | 25.7 | 1.67 s | | 14', 17' | 25.6 | 1.67 |
| 17' | 17.6 | 1.57 s | | 14', 16' | 17.6 | 1.58 |
| 18' | 195.1 | 9.35 s | | | 172.8 | |
| 19' | 16.1 | 1.63 s | | 8' | 15.8 | 1.60 |
| 20' | 16.0 | 1.64 s | | 2', 3' | 16.0 | 1.62 |

* not determined

TABLE 6

NMR data of compound represented by formula (6)

| | 5 | | | sargaquinoic acid | | | |
|---|---|---|---|---|---|---|---|
| # | $\delta_H$ | | J (Hz) | $\delta_C$ | $\delta_H$ | J (Hz) | HMBC (C) |
| 1 | | | | 187.9 | | | |
| 2 | | | | 148.4 | | | |
| 3 | 6.46 | dt | 1.6, 2.8 | 132.2 | 6.46 | dt | 1.6, 2.8 4, 5, 1' |
| 4 | | | | 188.0 | | | |
| 5 | 6.54 | dq | 2.8, 1.4 | 133.1 | 6.54 | dq | 2.8, 1.4 3, 4, 7 |
| 6 | | | | 145.9 | | | |
| 7 | 2.05 | d | 1.4 | 15.9 | 2.05 | d | 1.4 1, 5, 6 |
| 1' | 3.13 | br. d | 7.3 | 27.5 | 3.13 | br. d | 7.3 1, 2, 3, 2', 3' |
| 2' | 5.15 | overlapped | | 118.0 | 5.15 | overlapped | 1', 20' |
| 3' | | | | 139.7 | | | |
| 4' | 1.9~2.1 * | overlapped | | 39.5 | 2.1 * | overlapped | 2', 3', 5' |
| 5' | 1.9~2.1 * | overlapped | | 26.3 | 2.1 * | overlapped | 4', 6' |
| 6' | 5.1 * | overlapped | | 124.4 | 5.12 | overlapped | 5', 8', 19' |
| 7' | | | | 134.5 | | | |
| 8' | 1.9~2.1 * | overlapped | | 39.0 | 2.1 * | overlapped | 7', 9' |
| 9' | 1.9~2.1 * | overlapped | | 28.1 | 2.60 | dt | 7.3, 7.3 8', 10', 11' |
| 10' | 5.1 * | overlapped | | 145.1 | 6.01 | t | 7.3 8', 9', 12', 18' |
| 11' | | | | 130.7 | | | |
| 12' | 1.9~2.1 * | overlapped | | 34.5 | 2.26 | br. t | 7.6 10', 11', 13', 14', 18' |
| 13' | 1.9~2.1 * | overlapped | | 27.8 | 2.1 * | overlapped | 12', 14' |
| 14' | 5.1 * | overlapped | | 123.4 | 5.09 | overlapped | 13', 16', 17' |
| 15' | | | | 132.1 | | | |
| 16' | 1.67 | br. s | | 25.6 | 1.67 | br. s | 14', 15', 17' |
| 17' | 1.6 * | br. s | | 17.6 | 1.58 | br. s | 14', 15', 16' |
| 18' | 1.6 * | br. s | | 172.8 | | | |
| 19' | 1.6 * | br. s | | 15.8 | 1.60 | br. s | 6', 7', 8' |
| 20' | 1.62 | br. s | | 16.0 | 1.62 | br. s | 2', 3', 4' |

* not determined

From these NMR data, it was found that the compounds thus obtained are respectively represented by the formulas (1) to (6) described above.

2. Analysis of Anti-leishmanial Activity (1) Analysis of In Vitro Anti-leishmanial Activity The compounds represented by formulas (1) to (6), which had been isolated by the procedure described above, were subjected to an analysis of the physiological activity under the conditions that are described below. *Leishmania major* promastigotes were selected as the *Leishmania* protozoa, and a *L. major*/egfp promastigotes in which a fluorescent protein egfp gene had been introduced was used. The compounds mentioned above were used as samples. Thus, the growth inhibition rate was determined under the following conditions.

(Analysis Procedure)

*L. major*/egfp promastigotes were maintained at 25° C. using a 96-well plate, in 199 medium (NISSUI Pharmaceutical) containing 10% fetal bovine serum 25 mM and Hepes buffer (ICN Biomedeivals, Inc., Aurora, Ohio) and 10 µg/mL Tunicamycin (SIGMA-ALDRICH, inc., USA). Subsequently, to each well of 96-well plates containing 100 µL of *L. major*/egfp suspension with $1 \times 10^6$ cells/mL, 100 µL of test solution (sample dissolved in DMSO) was added, and the plates were incubated at 25° C. for 72 h. Thereafter, Fluorescence signals of *L. major*/egfp promastigotes were measured with a fluorescence microplate reader (Fluoroscan Ascent FL, Dainippon Pharmaceutical Co.) with excitation at 485 nm and emission at 538 nm. Furthermore, to determine the growth inhibition rate of *L. major*/egfp it is defined as 100% when Amphotericin B was used as the positive control, and the inhibition rate of various samples are presented.

Figure 9:
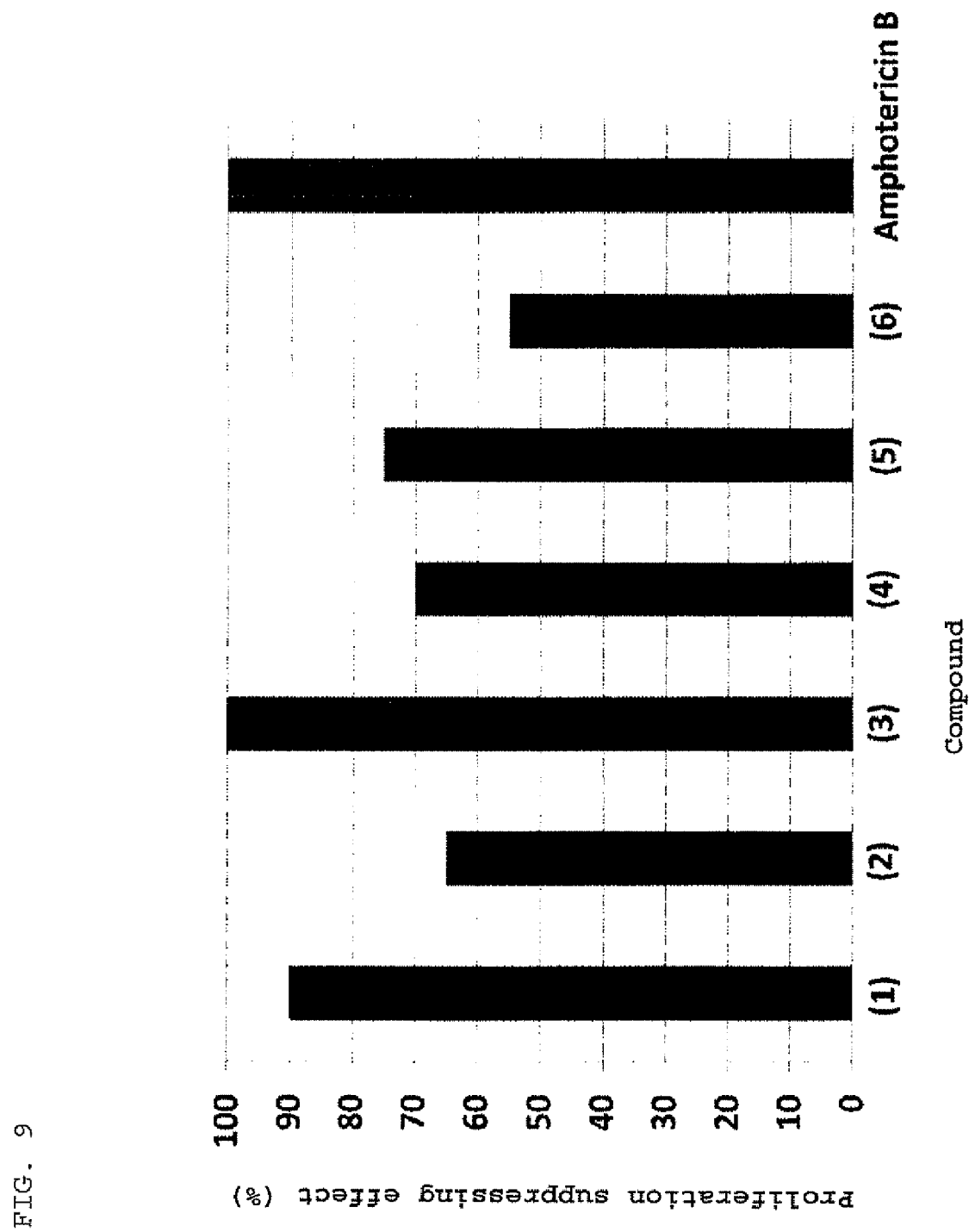
FIG. 9 is a graph showing the results of an in vitro anti-leishmanial activity analysis according to the Example of the present invention.

FIG. 9 shows the growth inhibition rate determined as a result of the analysis. According to these results, it was found that the compounds represented by the formulas (1) to (6) have a physiological activity characteristic of inhibiting the growth of the *Leishmania* protozoa. Particularly, the growth inhibition rate of the compound represented by formula (3)

was almost equal to the growth inhibition rate of Amphotericin B.

(2) Analysis of In Vivo Anti-leishmanial Activity

In order to evaluate the in vivo anti-leishmanial activity of the compound represented by formula (3), which had been isolated by the procedure described above, a leishmaniasis mouse model was used to investigate the therapeutic effect.

Six-week old mice (Balb/c, male, 6 animals per group) were infected with $1\times10^7$ cells of cultured promastigotes of *L. major* PM2. From the day after the infection day, the compound represented by the formula (3) was administered to each specimen in an amount of 200 [μg by peritoneal injection. The administration schedule was such that the compound was continuously administered once a day for three weeks. Further, as control, the same analysis was carried out also for a treatment group to which Amphotericin B was administered, and for a treatment group to which none was administered.

Figure 10:
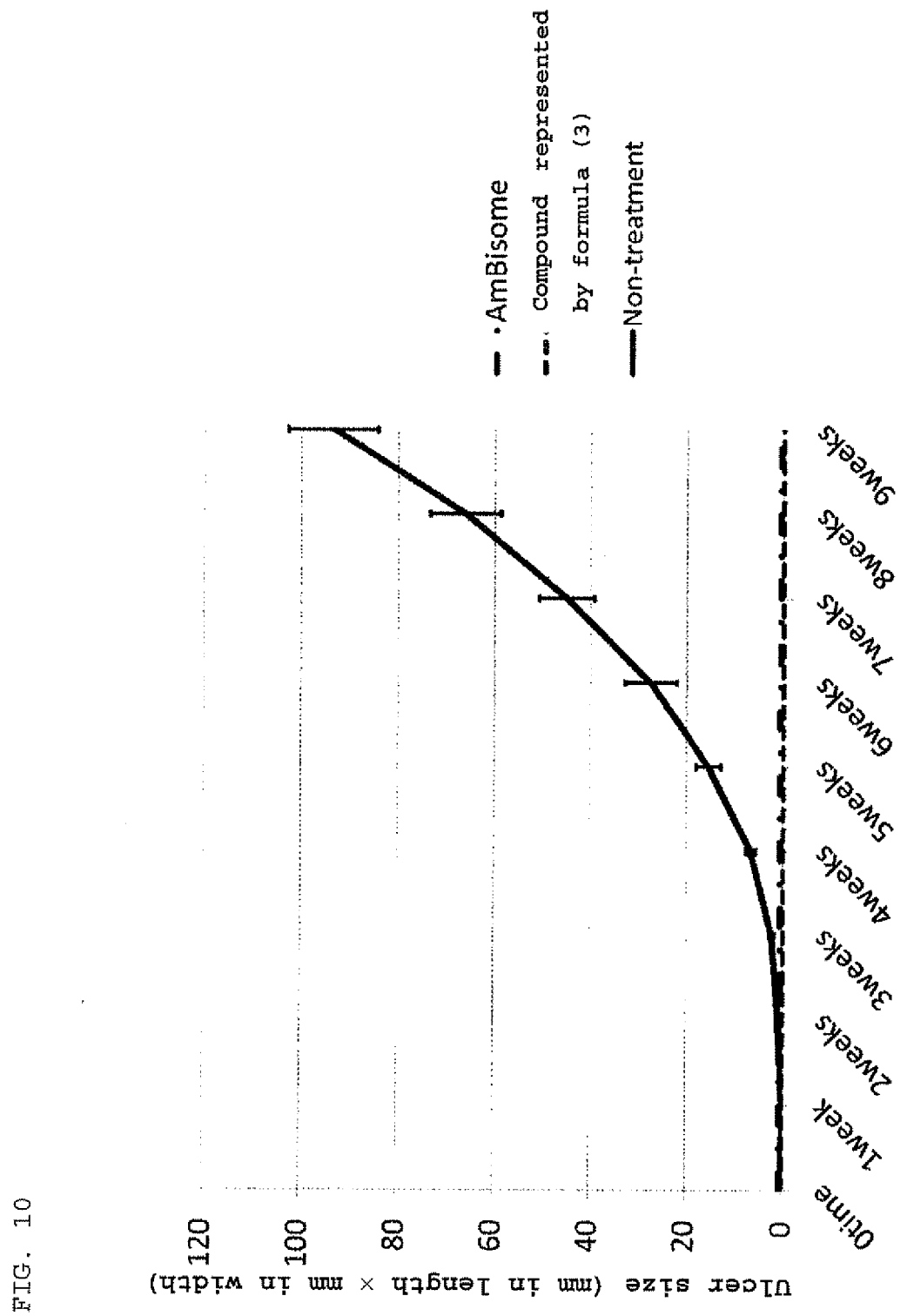
FIG. 10 is a graph showing the results of an in vivo anti-leishmanial activity analysis according to the Example of the present invention.
Figure 11:
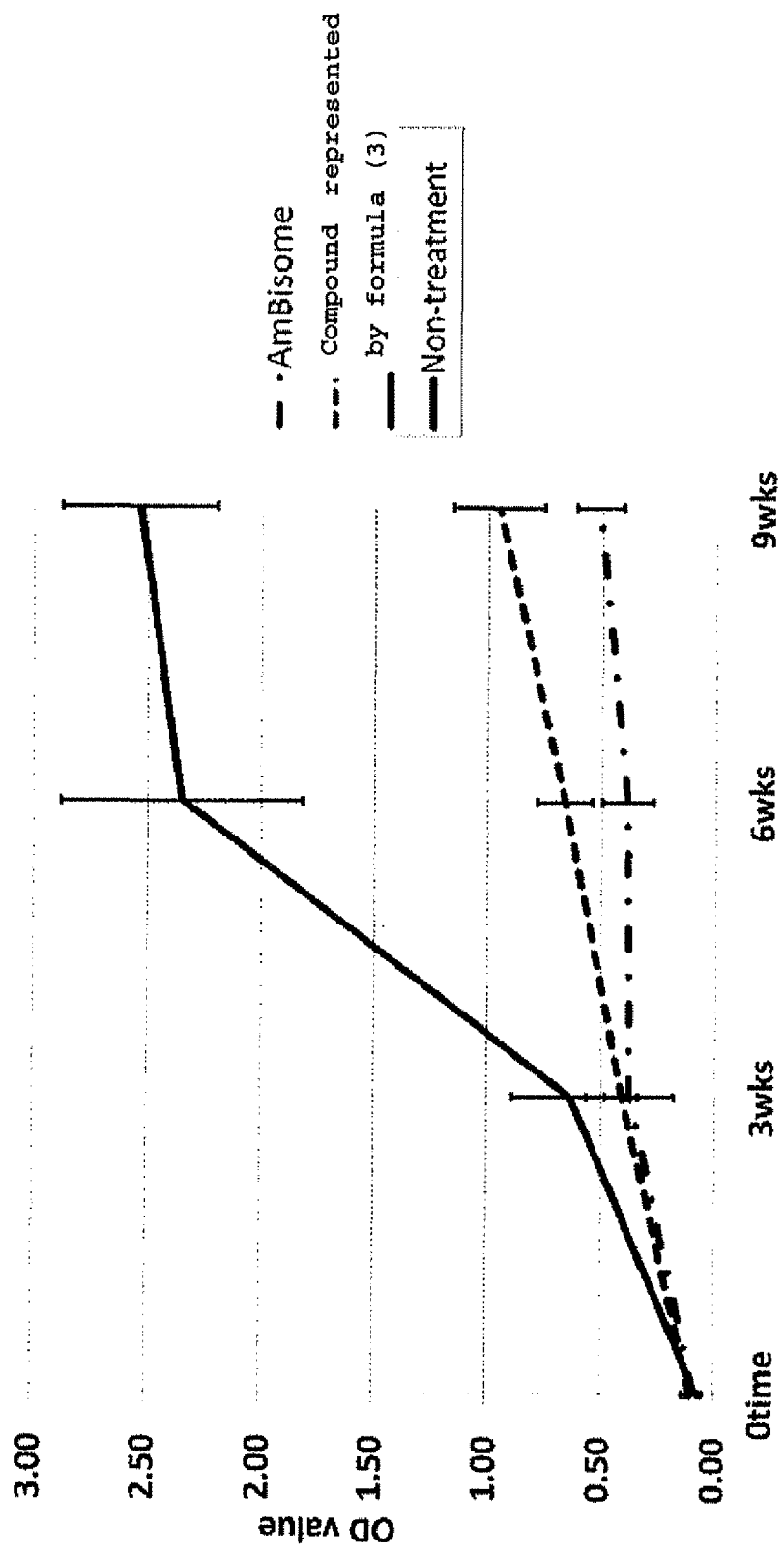
FIG. 11 is a diagram showing the results of an in vivo anti-leishmanial activity analysis according to the Example of the present invention.
Figure 12:
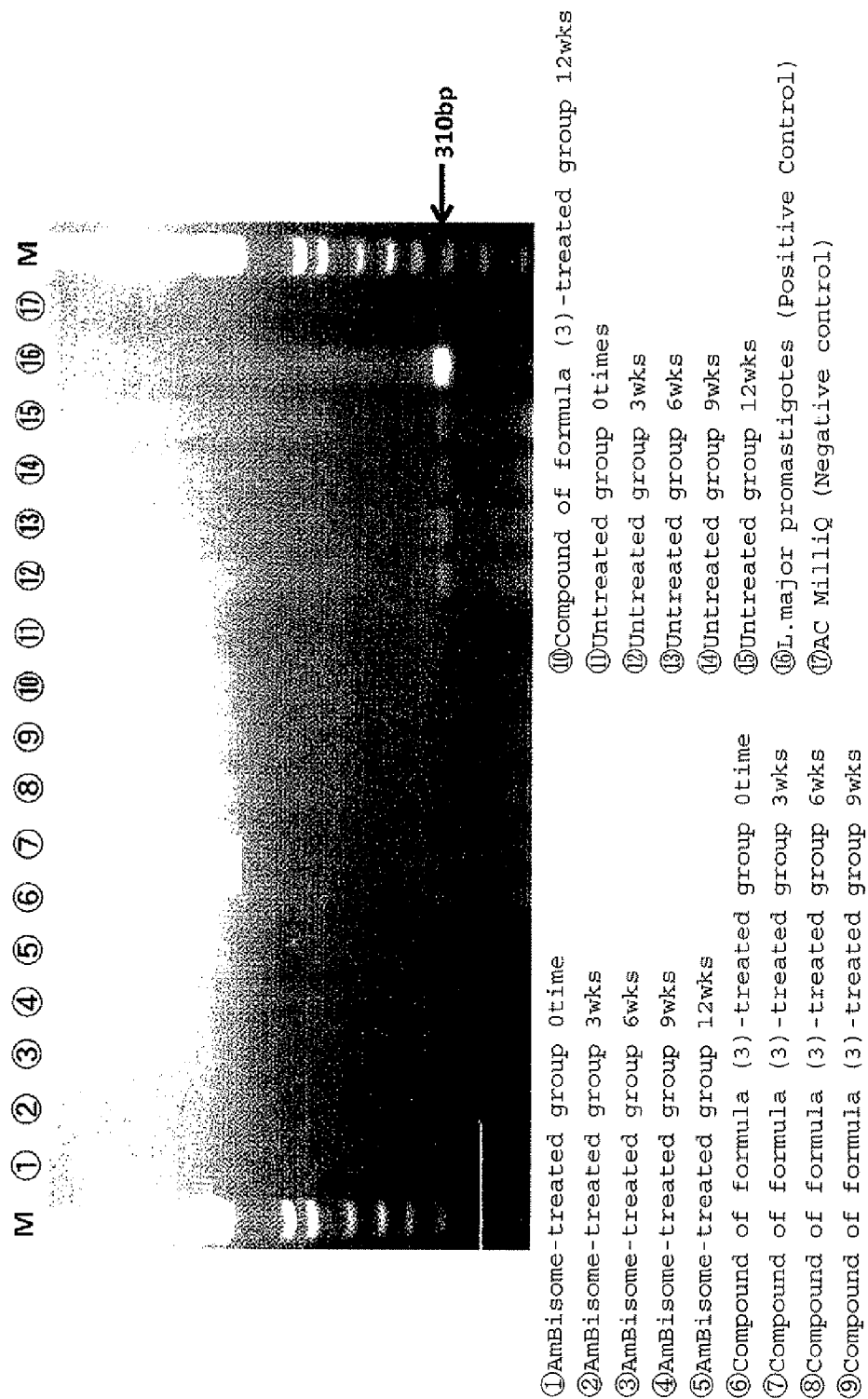
FIG. 12 is a diagram showing the results of an in vivo anti-leishmanial activity analysis according to the Example of the present invention.

The results obtained by measuring the size of ulcer in the mice are presented in FIG. 10. Furthermore, FIG. 11 shows the fluctuation of antibody titer in blood of the mice. FIG. 12 shows the results obtained by performing electrophoresis of a DNA product which has been amplified by PCR carried out using the DNA extracted from the mouse blood as a template and using the protozoan gene as a target. That is, FIG. 12 shows the results for the detection of the protozoan DNA in blood, and when the protozoan DNA is present, a PCR product is observed at the position of 310 bp. As the white color becomes more intense in FIG. 12, it shows that the protozoan DNA is present at a higher concentration. On the other hand, when the position of 310 by is black, it shows that the protozoan DNA is not present.

From these results, it was found that the compound represented by the formula (3) exhibits an anti-leishmanial activity that is equal to that of Amphotericin B, even in vivo.

The invention claimed is:

1. An isolated anti-leishmanial compound represented by formula (3):

{Chem. 3}

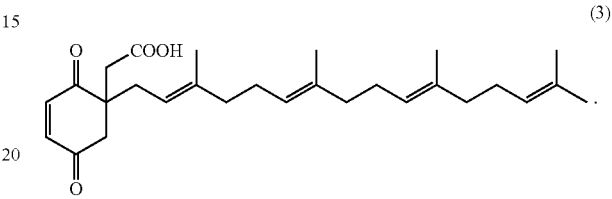

(3)

2. An anti-leishmanial drug comprising the isolated anti-leishmanial compound according to claim 1 or a pharmacologically acceptable salt thereof as an active ingredient.

* * * * *

UNITED STATES PATENT AND TRADEMARK OFFICE
CERTIFICATE OF CORRECTION

PATENT NO. : 8,373,006 B2  
APPLICATION NO. : 13/146366  
DATED : February 12, 2013  
INVENTOR(S) : Junji Kimura et al.

Page 1 of 1

It is certified that error appears in the above-identified patent and that said Letters Patent is hereby corrected as shown below:

Title Page, (75) Inventors should read: Junji Kimura, Sagamihara (JP); Shohei Horie, Ibaraki (JP); Harumi Marushima, Yokosuka (JP); Yoshitsuga Matsumoto, Taito-Ku (JP); Chizu Sanjoba, Kawaguchi (JP); Yasutaka Osada, Bunkyo-Ku (JP)

Signed and Sealed this  
Ninth Day of April, 2013

Teresa Stanek Rea  
*Acting Director of the United States Patent and Trademark Office*